US012060439B2

(12) United States Patent
Hughes et al.

(10) Patent No.: US 12,060,439 B2
(45) Date of Patent: Aug. 13, 2024

(54) POLYMORPH OF ECHINOCANDIN ANTIFUNGAL AGENT

(71) Applicant: Cidara Therapeutics, Inc., San Diego, CA (US)

(72) Inventors: Martin Patrick Hughes, Spokane, WA (US); Robert Michael Hughes, San Diego, CA (US); Yannick Borguet, Waringstown (GB); Cen Chen, Suzhou (CN); Jianwei Shen, Jinan (CN); Alan Thompson, Lawrencetown (GB); Tracy Walker, Dollingstown (GB); Yanfeng Zhang, Suzhou (CN)

(73) Assignee: Napp Pharmaceutical Group Limited, Cambridge (GB)

( * ) Notice: Subject to any disclaimer, the term of this patent is extended or adjusted under 35 U.S.C. 154(b) by 300 days.

(21) Appl. No.: 17/288,172

(22) PCT Filed: Oct. 25, 2019

(86) PCT No.: PCT/US2019/058007
§ 371 (c)(1),
(2) Date: Apr. 23, 2021

(87) PCT Pub. No.: WO2020/086931
PCT Pub. Date: Apr. 30, 2020

(65) Prior Publication Data
US 2021/0355165 A1    Nov. 18, 2021

Related U.S. Application Data

(60) Provisional application No. 62/756,930, filed on Nov. 7, 2018.

(30) Foreign Application Priority Data

Oct. 25, 2018  (CN) .......................... 201811254080.8

(51) Int. Cl.
C07K 7/64       (2006.01)
C07K 1/30       (2006.01)
C07K 1/34       (2006.01)

(52) U.S. Cl.
CPC .............. *C07K 7/64* (2013.01); *C07K 1/306* (2013.01); *C07K 1/34* (2013.01); *C07B 2200/13* (2013.01)

(58) Field of Classification Search
None
See application file for complete search history.

(56) References Cited

U.S. PATENT DOCUMENTS

| | | |
|---|---|---|
| 5,965,525 A | 10/1999 | Burkhardt et al. |
| 8,722,619 B2 | 5/2014 | James, Jr. et al. |
| 9,006,391 B2 | 4/2015 | De Pater et al. |
| 9,217,014 B2 | 12/2015 | James, Jr. et al. |
| 9,526,835 B2 | 12/2016 | Radhakrishnan et al. |
| 9,676,821 B2 | 6/2017 | James, Jr. et al. |
| 10,016,479 B2 | 7/2018 | Radhakrishnan et al. |
| 10,369,188 B2 | 8/2019 | Bartizal et al. |
| 10,702,573 B2 | 7/2020 | Radhakrishnan et al. |
| 10,780,144 B2 | 9/2020 | Bartizal et al. |
| 2002/0161176 A1 | 10/2002 | Dalder et al. |
| 2009/0291996 A1 | 11/2009 | Korodi et al. |
| 2013/0030149 A1 | 1/2013 | Rastogi et al. |
| 2016/0075740 A1 | 3/2016 | James, Jr. et al. |
| 2017/0198013 A1 | 7/2017 | Liu et al. |
| 2017/0253635 A1 | 9/2017 | James, Jr. et al. |
| 2018/0256673 A1 | 9/2018 | Balkovec et al. |
| 2019/0216885 A1 | 7/2019 | Bartizal et al. |
| 2019/0307843 A1 | 10/2019 | Bartizal et al. |
| 2019/0374601 A1 | 12/2019 | Bartizal et al. |
| 2020/0164023 A1 | 5/2020 | Bartizal et al. |
| 2020/0268833 A1 | 8/2020 | Bartizal et al. |
| 2021/0002346 A1 | 1/2021 | Bartizal et al. |
| 2021/0128670 A1 | 5/2021 | Radhakrishnan et al. |

FOREIGN PATENT DOCUMENTS

| | | |
|---|---|---|
| EP | 2261237 B1 | 8/2018 |
| WO | WO-2008/048627 A1 | 4/2008 |
| WO | WO-2010/108637 A1 | 9/2010 |
| WO | WO-2012/119065 A2 | 9/2012 |
| WO | WO-2013/142279 A1 | 9/2013 |
| WO | WO-2015/035102 A2 | 3/2015 |
| WO | WO-2016/056022 A2 | 4/2016 |
| WO | WO 2016201283 * | 12/2016 |
| WO | WO-2017/049102 A1 | 3/2017 |
| WO | WO-2017/049105 A1 | 3/2017 |
| WO | WO-2017/120471 A1 | 7/2017 |
| WO | WO-2017/161016 A1 | 9/2017 |
| WO | WO-2018/085200 A1 | 5/2018 |
| WO | WO-2018/102407 A1 | 6/2018 |
| WO | WO-2018/144600 A1 | 8/2018 |
| WO | WO-2018/187574 A1 | 10/2018 |

(Continued)

OTHER PUBLICATIONS

International Preliminary Report on Patentability and Written Opinion for International Application No. PCT/US2019/58007, mailed Jun. 20, 2020 (23 pages).

International Search Report and Written Opinion for International Application No. PCT/US2019/58007, mailed Jan. 2, 2020 (20 pages).

Krishnan et al., "CD101, a novel echinocandin with exceptional stability properties and enhanced aqueous solubility," J Antibiot (Tokyo). 70(2):130-135 (2017).

(Continued)

*Primary Examiner* — Thomas S Heard

(74) *Attorney, Agent, or Firm* — Clark & Elbing LLP

(57) ABSTRACT

The present invention relates to crystalline polymorphs of an echinocandin antifungal agent and novel methods for their preparation.

5 Claims, 9 Drawing Sheets

(56) References Cited

FOREIGN PATENT DOCUMENTS

| WO | WO-2018/191692 A1 | 10/2018 |
| WO | WO-2019/014333 A1 | 1/2019 |
| WO | WO-2019/027498 A1 | 2/2019 |
| WO | WO-2020/086931 A1 | 4/2020 |

OTHER PUBLICATIONS

U.S. Appl. No. 17/023,884, filed Sep. 17, 2020 (42 pages).
U.S. Appl. No. 17/029,784, filed Sep. 23, 2020 (75 pages).
U.S. Appl. No. 17/365,188 filed Jul. 1, 2021 (52 pages).
U.S. Appl. No. 17/252,579, filed Dec. 15, 2020 (20 pages).

\* cited by examiner

POLYMORPH OF ECHINOCANDIN ANTIFUNGAL AGENT

BACKGROUND

This invention features novel crystalline forms of an echinocandin antifungal agent and novel methods for preparing them. The invention also features novel methods for isolating an amorphous form of an echinocandin antifungal agent.

Fungal infections, such as those caused by *Candida* and *Aspergillus*, can be serious and life-threatening infections that represent a significant public health issue, particularly in highly vulnerable populations including the elderly, post-surgical, critically ill, and other hospitalized patients with serious medical conditions. Because of increasing resistance to existing antifungal drugs, there is an urgent need to develop new and more effective antifungal agents to treat these serious infections. Echinocandins are members of a leading class of antifungal agents for the treatment of fungal infections. These compounds target the cell wall by preventing the production of 1,3-β-D-glucan through inhibition of the catalytic subunit of 1,3-β-D-glucan synthase enzyme complex.

Crystalline forms of pharmaceutical grade echinocandins or salts thereof could benefit the stability of these compounds. Crystalline forms are generally more stable and easier to handle than amorphous forms. Additionally, crystallization processes may help further optimize the purity of the echinocandin antifungal agent. Thus, there is a need for novel polymorphs of echinocandins and reproducible methods of synthesizing these polymorphs of echinocandins.

SUMMARY OF THE INVENTION

The present invention features new polymorphs of compound 1 acetate which exhibit improved physical properties. In particular, the invention features different polymorph forms of compound 1 acetate that are classified as Type A, B, C, D, E, G, or H.

In an aspect, the invention features a solid crystalline form of compound 1 acetate having an X-ray powder diffraction (XRPD) pattern including angles 2θ (°) of 7.1±0.2, 9.2±0.2, and 13.7±0.2.

In some embodiments, the XRPD pattern further includes one or more angles 2θ (°) selected from the group consisting of 7.8±0.2, 8.3±0.2, 10.5±0.2, 14.9±0.2, 16.6±0.2, 17.6±0.2, 19.4±0.2, 20.5±0.2, 22.7±0.2, and 27.5±0.2.

In another aspect, the invention features a solid crystalline form of compound 1 acetate having an X-ray powder diffraction (XRPD) pattern including angles 2θ (°) of 6.8±0.2, 7.4±0.2, 8.2±0.2, and 9.5±0.2.

In some embodiments, the XRPD pattern further includes one or more angles 2θ (°) selected from the group consisting of 10.1±0.2, 13.5±0.2, 15.0±0.2, 20.0±0.2, 20.3±0.2, and 21.9±0.2.

In another aspect, the invention features a solid crystalline form of compound 1 acetate having an X-ray powder diffraction (XRPD) pattern including angles 2θ (°) of 3.2±0.2 and 6.2±0.2.

In some embodiments, the XRPD pattern further includes one or more angles 2θ (°) selected from the group consisting of 9.3±0.2, 12.3±0.2, 15.5±0.2, 17.9±0.2, 18.5±0.2, 19.4±0.2, and 21.6±0.2.

In another aspect, the invention features a solid crystalline form of compound 1 acetate having an X-ray powder diffraction (XRPD) pattern including angles 2θ (°) of 6.0±0.2 and 8.7±0.2.

In some embodiments, the XRPD pattern further includes one or more angles 2θ (°) selected from the group consisting of 10.6±0.2, 14.7±0.2, 14.9±0.2, 15.3±0.2, 15.5±0.2, 17.2±0.2, 18.9±0.2, 19.7±0.2, 20.0±0.2, 21.5±0.2, 21.6±0.2, 21.8±0.2, 22.4±0.2, and 23.7±0.2.

In an aspect, the invention features a pharmaceutical composition including any of the foregoing solid crystalline forms of compound 1 acetate and a pharmaceutically acceptable excipient.

In an aspect, the invention features a method of purifying compound 1 acetate from a mixture including compound 1 acetate and compound 1 acetate beta-diastereomer, the method including: (i) dissolving the mixture in an organic solvent to form a solution; and (ii) cooling the solution and/or evaporating the organic solvent to produce crystals of compound 1 acetate.

In some embodiments, the crystals of compound 1 acetate include the solid crystalline form of any of the foregoing solid crystalline forms of compound 1 acetate.

In an aspect, the invention features a method of producing any of the foregoing solid crystalline forms of compound 1 acetate, the method including (i) dissolving the mixture in an organic solvent to form a solution; and (ii) cooling the solution and/or evaporating the organic solvent to produce crystals of compound 1 acetate.

In some embodiments, the percent (w/w) of compound 1 acetate beta-diastereomer in the crystals is reduced relative to the percent (w/w) of compound 1 acetate beta-diastereomer in the mixture.

In some embodiments, the organic solvent is selected from ethanol, acetonitrile, methyl ethyl ketone, 2-methyltetrahydrofuran, 1-butanol, isobutanol, or any combination thereof.

In some embodiments, the organic solvent is ethanol.

In some embodiments, the organic solvent is anhydrous. In other embodiments, the organic solvent is a mixture with water.

In some embodiments, the organic solvent is anhydrous ethanol or a mixture of ethanol and water.

In an aspect, the invention features a method of isolating compound 1 acetate, said method comprising: (i) dissolving compound 1 acetate in organic solvent comprising a molar excess of acetate salt; (ii) precipitating compound 1 acetate by addition of an anti-solvent; and (iii) filtering to recover compound 1 acetate as a solid material.

In some embodiments, dissolving compound 1 acetate in organic solvent further comprises extracting compound 1 acetate into organic solvent from an aqueous solution containing an acetate salt prior to step (ii).

In some embodiments, the acetate salt is selected from ammonium acetate, sodium acetate, and potassium acetate.

In some embodiments, the organic solvent is selected from any one of 1-butanol, 2-butanol, isobutanol, methyl ethyl ketone, isobutyl methyl ketone, 2-methyltetrahydrofuran, or any combination thereof.

In some embodiments, the anti-solvent is selected from methyl tert-butyl ether, ethyl tert-butyl ether, 2-methyltetrahydrofuran, isobutyl methyl ketone, toluene, heptanes, and hexanes.

Definitions

As used herein, the terms "anhydrous solvent system" and "solvent system is anhydrous" refer to a solvent system that is dried prior to use in the reaction and/or that contains less than 0.1% of water. For example, "anhydrous acetonitrile" and "acetonitrile is anhydrous" each refers to acetonitrile that is dried prior to use in the reaction and/or acetonitrile that contains less than 0.1% of water.

As used herein, the term "compound 1" refers to the compound having the structure shown below. The term "compound 1 in salt form" or "a salt of compound 1" refers to compound 1 when its tertiary ammonium ion positive charge is balanced with a negative counterion (e.g., an acetate).

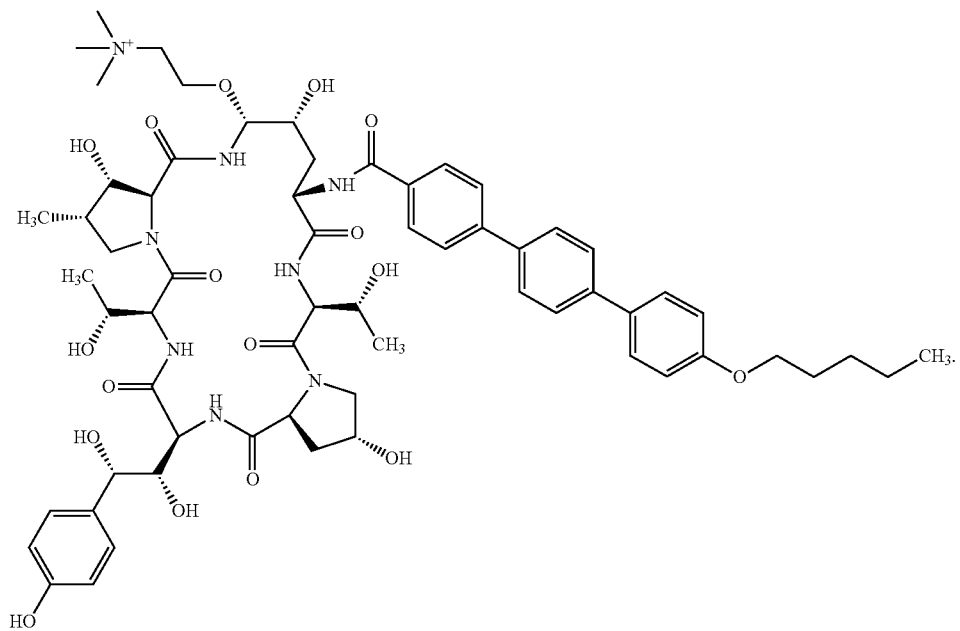
(compound 1)
As used herein, the term "compound 1 acetate" refers to the acetate salt of compound 1 and has the structure as shown below.
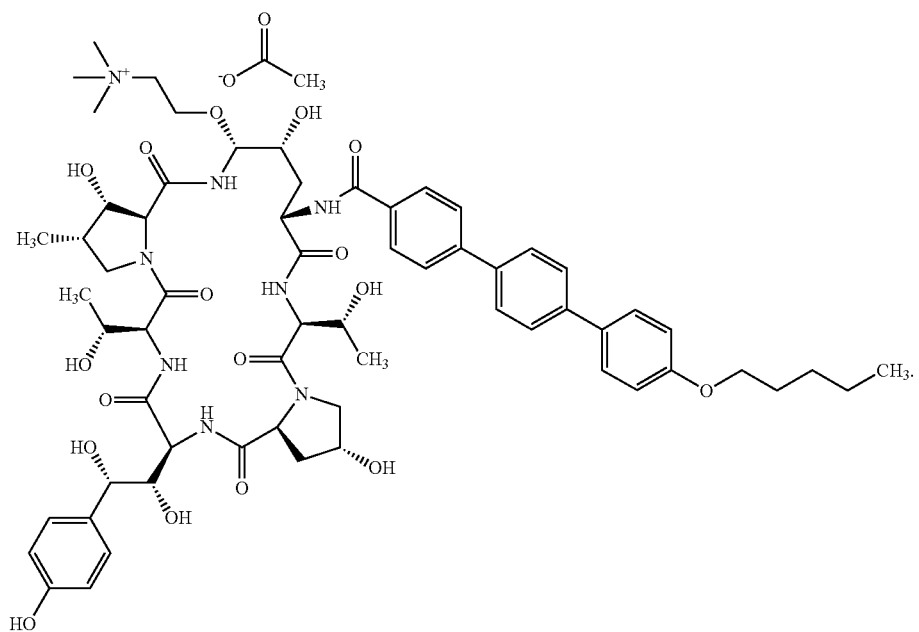
(compound 1 acetate)

As used herein, the terms "compound 1 acetate beta-diastereomer" and "beta-diastereomer" refer to the structure as shown below.
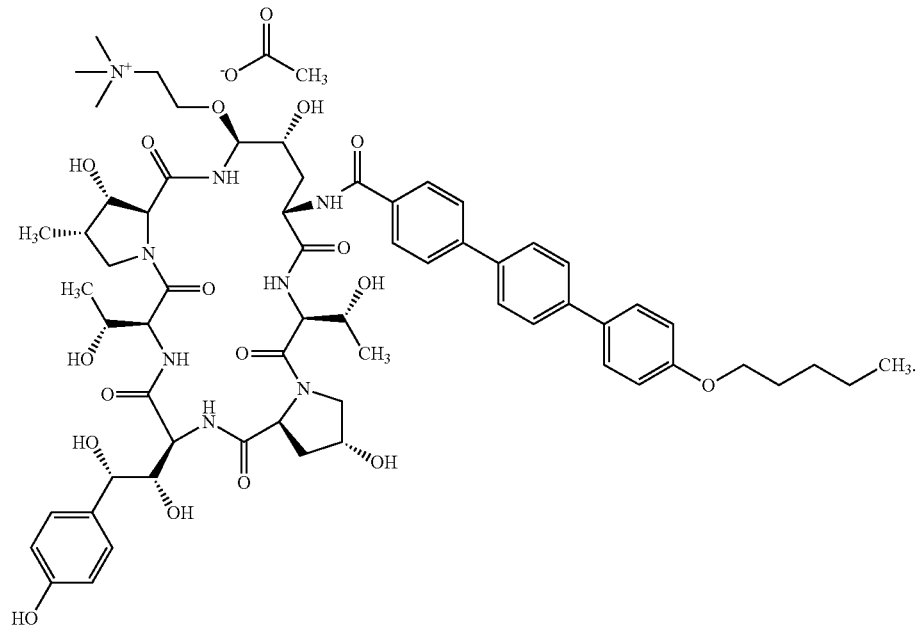
(compound 1 acetate beta-diastereomer)
As used herein, the terms "compound 1 acetate epimer" and "epimer" refer to the structure as shown below.
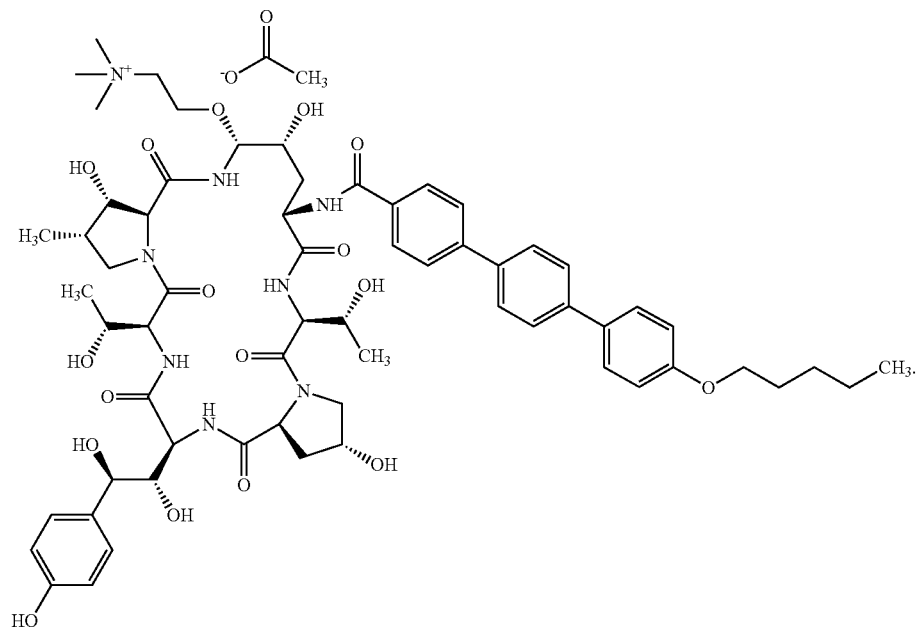
(compound 1 acetate epimer)

As used herein, the term "echinocandin-containing" refers to compound 1, compound 1 acetate, compound 1 acetate beta-diastereomer, and/or compound 1 acetate epimer. For example, "echinocandin-containing reaction product" may refer to a reaction product that includes compound 1 acetate and compound 1 acetate beta-diastereomer, and/or compound 1 acetate epimer.

As used herein, the term "about" refers to a range of values that is ±10% of specific value. For example, "about 150 mg" includes ±10% of 150 mg, or from 135 mg to 165 mg. Such a range performs the desired function or achieves the desired result. For example, "about" may refer to an amount that is within less than 10% of, within less than 5% of, within less than 1% of, within less than 0.1% of, and within less than 0.01% of the stated amount.

As used herein, the terms "infection" and "fungal infection" refer to a microbial dysbiosis characterized by overgrowth or colonization of any part of the body of a human subject by one or more species of fungi (e.g., fungal pathogens or opportunistic pathogens), reduction of which may provide benefit to the host. For example, the infection may include the excessive growth of or colonization by fungal species that are normally present in or on the body of a human subject, or the infection may include colonization by fungal species that are not normally present in or on the body of a human subject. In some instances, the infection may include colonization of a part of the body by a fungus that is indigenous to some parts of the human body (e.g., GI tract) but is detrimental when found in other parts of the body (e.g., tissues beyond the GI tract). More generally, an infection can be any situation in which the presence of a microbial population(s) is damaging to a host body.

Other features and advantages of the invention will be apparent from the following detailed description and the claims.

DETAILED DESCRIPTION

Figure 1:
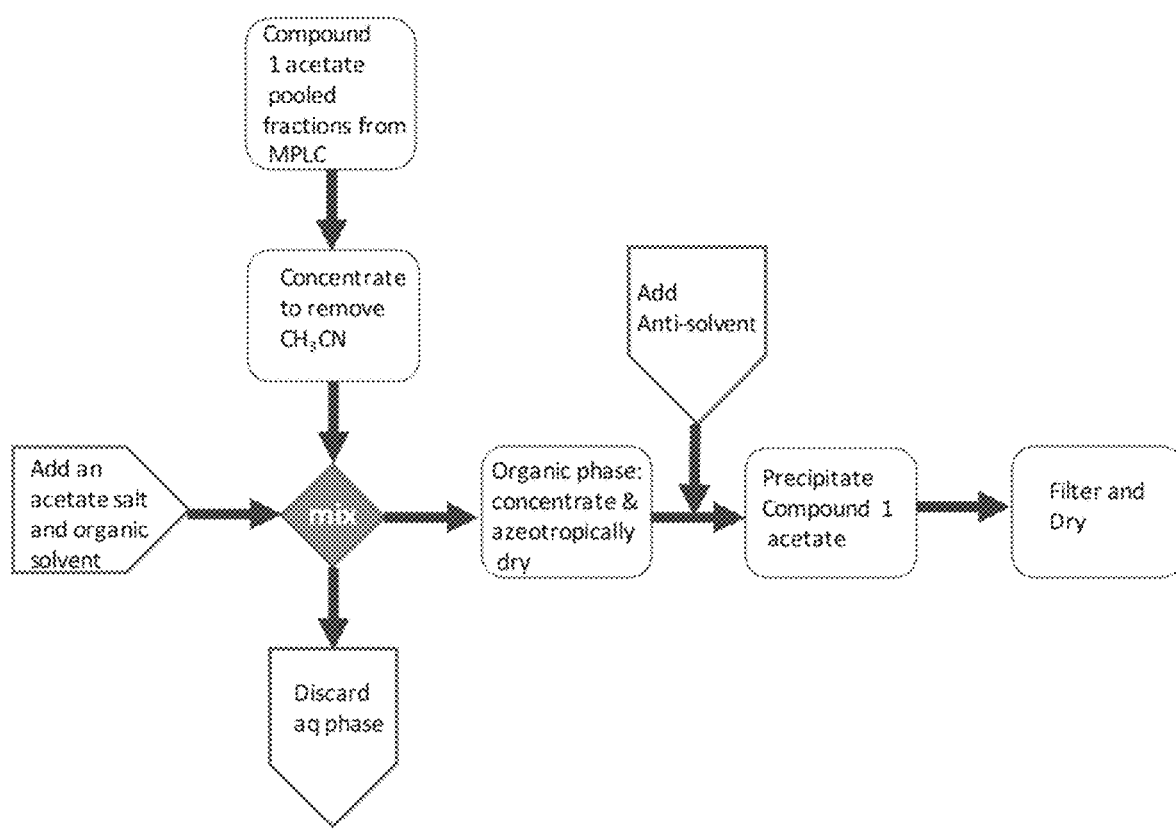
FIG. 1 is a scheme depicting the isolation of compound 1 acetate by extraction and precipitation processes.

Provided herein are novel crystalline polymorphs of compound 1 acetate and methods of synthesizing the polymorphs. The methods can be useful for achieving higher purity of compound 1 acetate from an echinocandin-containing mixture. Further characterization of the polymorphs and procedures to synthesize the polymorphs are provided in the Examples.

To identify compound 1 acetate polymorphs with improved properties (e.g., less hygroscopic, improved stability, and/or higher purity), polymorph screening of compound 1 acetate was conducted.

Compound 1 acetate, and its polymorphs, can be useful for treating, mitigating, or preventing a fungal infection or related conditions thereto in a human subject in need thereof.

Compound 1 acetate, and its polymorphs, may be used to prepare a pharmaceutical composition. The pharmaceutical composition can include compound 1 acetate and pharmaceutically acceptable carriers and excipients. The pharmaceutical composition can be formulated for subcutaneous injection or intravenous infusion or topical applications. Depending on the mode of administration (e.g., subcutaneously, intravenously, or topically) and the dosage, compound 1 acetate may be formulated into suitable pharmaceutical compositions to permit facile delivery. A summary of such techniques is found in Remington: The Science and Practice of Pharmacy, 22nd Edition, Lippincott Williams & Wilkins, (2012); and Encyclopedia of Pharmaceutical Technology, eds. J. Swarbrick and J. C. Boylan, 2006, Marcel Dekker, New York, each of which is incorporated herein by reference.

For subcutaneous administration, compound 1 acetate may be formulated as an aqueous pharmaceutical composition. In some embodiments, the pharmaceutical composition containing compound 1 formulated for subcutaneous administration may not contain a buffer. In some embodiments, the pharmaceutical composition formulated for subcutaneous administration may contain a weak buffer. Examples of a weak buffer that may be used in the pharmaceutical composition include, but are not limited to, acetate, lactate, histidine, glycine, and formate.

A pharmaceutical composition including compound 1 acetate salt may optionally contain an amount of a solubilizing agent. Examples of a solubilizing agent include, but are not limited to, polysorbate 20 (Tween 20; polyoxyethylene (20) sorbitan monolaurate), polysorbate 40 (Tween40; polyoxyethylene (40) sorbitan monopalmitate), polysorbate 60 (Tween 60; polyoxyethylene (60) sorbitan monostearate), polysorbate 80 (Tween 80; polyoxyethylene (80) sorbitan monooleate), β-cyclodextrin, polyoxyl 35 castor oil (Cremophor EL), polyoxyl 40 hydrogenated castor oil (Cremophor RH 40), polyoxyl 60 hydrogenated castor oil (Cremophor RH 60), D-α-tocopheryl polyethylene glycol 1000 succinate (TPGS), sorbitan monooleate (Span 20), polyoxyl 8 stearate (PEG 400 monsterate), polyoxyl 40 stearate (PEG 1750 monsterate), PEG 400 caprylic/capric glycerides (Labrasol), PEG 300 oleic glycerides (Labrafil M-1944CS), phosphatidylcholine (lecithin), alkylglucoside, sucrose monolaurate, sucrose monooleate, and polyoxyethylene-polyoxypropylene block copolymer (Poloxamer).

Furthermore, a pharmaceutical composition including compound 1 acetate may contain between 0.5% to 3% (w/w) of a saccharide. Examples of a saccharide that may be included in the pharmaceutical composition including compound 1 acetate used in the methods of the invention include, but are not limited to, mannitol, sucrose, trehalose, fructose, glucose, dextrose, dextran, lactose, and sorbital.

A pharmaceutical composition including compound 1 acetate may be formulated as a lyophilized composition. Moreover, the lyophilized composition including compound 1 acetate when re-constituted in water for injection, may have a pH of between 5 and 6.5 (e.g., about 5, about 5.3, about 5.6, about 5.9, about 6.2, or about 6.5).

The pharmaceutical compositions used in the methods of the invention may be formulated in the form of liquid solutions or suspensions or lyophilized cakes and administered by a parenteral route (e.g., subcutaneous or intravenous), or in the form of gels, creams or ointments administered topically. Pharmaceutical compositions for parenteral administration can be formulated using a sterile solution or any pharmaceutically acceptable liquid as a vehicle. Pharmaceutically acceptable vehicles include, but are not limited to, sterile water, physiological saline, or cell culture media (e.g., Dulbecco's Modified Eagle Medium (DMEM), α-Modified Eagles Medium (α-MEM), F-12 medium). Formulation methods are known in the art, see e.g., Gibson (ed.) Pharmaceutical Preformulation and Formulation (2nd ed.) Taylor & Francis Group, CRC Press (2009).

Furthermore, acceptable carriers and excipients in the pharmaceutical composition used in methods of the invention are nontoxic to recipients at the dosages and concentrations employed. Acceptable carriers and excipients may include buffers such as phosphate, citrate, histidine, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. The compositions may be formulated according to conventional pharmaceutical practice. The concentration of the compound in the formulation will vary depending upon a number of factors, including the dosage of the drug to be administered, and the route of administration.

The pharmaceutical compositions of the invention can be administered to human subjects in therapeutically effective amounts. The preferred dosage of drug to be administered is likely to depend on such variables as the type and extent of the disorder, the overall health status of the particular human subject, the specific compound being administered, the excipients used to formulate the compound, and its route of administration.

The timing of the administration of the pharmaceutical composition containing compound 1 acetate depends on the medical and health status of the human subject. In some instances, the human subject is at risk for developing a fungal infection or a related condition and receives one or more doses treatment with compound 1 acetate before developing symptoms or signs of a fungal infection. In some instances, the human subject has already developed a fungal infection or a related condition and receives one or more doses treatment with compound 1 acetate. The timing of the administration of the dose(s) of compound 1 acetate may be optimized by a physician to reduce the risk of or to treat a fungal infection in a human subject.

The following examples, as set forth below, are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLES

Example 1. Isolation of Compound 1 Acetate by Precipitation

As an alternative to lyophilization, a precipitation process was developed to isolate compound 1 acetate. The process involves extraction of the HPLC, MPLC, or ion exchange chromatography pooled fractions into an organic solvent, drying, then precipitation with an anti-solvent to generate compound 1 acetate as shown in FIG. 1.

The pooled fractions from the HPLC, MPLC, or ion exchange chromatography purification are concentrated to remove most of the acetonitrile. Then the aqueous layer is salted with an acetate salt (ammonium acetate, potassium acetate or sodium acetate). An organic solvent is added and the two layers mixed. Suitable organic solvents include alcohols (1-BuOH, 2-BuOH, i-BuOH, 2-phenylethanol, t-amyl alcohol, isoamyl alcohol, benzyl alcohol), and the solvents methyl ethyl ketone, and 2-methyltetrahydrofuran. The layers are allowed to settle and are separated. The aq. layer may be extracted once or twice further. The organic layers are then combined and concentrated under vacuum to reduce volume as well as reduce the water content via azeotropic drying. During the concentration and drying step compound 1 acetate may start to precipitate. An anti-solvent may be added to complete precipitation. Suitable anti-solvents include methyl t-butyl ether (MTBE), ethyl t-butyl ether, heptanes, hexanes, methyl acetate, ethyl acetate, isopropyl acetate, 2-methyltetrahydrofuran, isobutyl methyl ketone, methyl ethyl ketone, and toluene.

Example 2. General Methods to Generate Crystalline Polymorphs of Compound 1 Acetate Temperature Cycling Samples of compound 1 acetate were weighed into glass vials and a known volume of solvent was added to each. The vials were capped and placed in a temperature controlled workstation. The workstation was cycled between 5-40° C. with varying heating and cooling rates. The samples were then removed, and the solids were isolated and analyzed by XRPD.

Vapor Stress

Samples of compound 1 acetate were weighed into glass vials, which remained uncapped, and placed inside a larger vial containing a volatile solvent or solvent mixture. The larger vials were capped, and the samples were left undisturbed for a period of time prior to analysis by XRPD.

Vapor Diffusion

Samples of compound 1 acetate were weighed into glass vials and combined with solvents. The mixtures were agitated to aid dissolution and then filtered using 0.2 µm nylon filters into clean vials. The vials remained uncapped and were then placed inside larger vials containing a volatile solvent or solvent mixture. The larger vials were capped, and the samples were left undisturbed for a period of time prior to analysis by XRPD.

Slurry

Samples of compound 1 acetate were weighed into glass vials and a known volume of solvent added. The vials were capped and stirred at a set temperature for a period of time before isolation and analysis of solids by XRPD.

Precipitation with Anti-Solvent

Compound 1 acetate was added to a vial and a solvent mixture was added to form a solution. The solution was then added to a vial containing anti-solvent and then stirred for about 10 minutes. Further addition of anti-solvent also used if precipitation was not initially seen. If no precipitate was observed, the vial was placed in the freezer.

Slow Evaporation

Compound 1 acetate was added to a glass vial and dissolved in a solvent or a solvent mixture. The mixture was agitated to aid dissolution and filtered with 0.2 μm nylon filter into a clean vial. The vials were covered with Parafilm®, perforated, and the solvent was allowed to evaporate under ambient conditions.

Recrystallization

Samples of compound 1 acetate were dissolved in a EtOH or EtOH/water mixture and stirred at ambient temperature. In some cases, an anti-solvent was added. In some experiments, crystalline seeds were added to help induce crystallization.

Example 3. Determining Solvent Activity

Compound 1 acetate and a solvent or solvent mixture were added to a vial and stirred at ambient temperature overnight to form a saturated suspension. Ethanol (EtOH) activity (aEtOH) of the solvent or solvent mixture was calculated using UNIFAC software. A further aliquot of the solvent or solvent mixture was added to the vial if the mixture was very thick. If all solids had dissolved, further amounts of compound 1 acetate were added and the mixture was stirred overnight. The slurry was then seeded with compound 1 acetate and compound 1 acetate-EtOH solvate and allowed to stir at ambient temperature for several days before isolation of solids and analysis by XRPD.

Example 4. Summary of Compound 1 Acetate Polymorph Screening

During the crystallization screen a number of unique solids were isolated that exhibited crystallinity and were classified as Type A, B, C, D, E, G, or H (Table 1).

TABLE 1

| Entry No. | Solvent or Solvent Mixture | Screening method | XRPD Result |
|---|---|---|---|
| 1 | EtOH | Temperature Cycling: 5° C. to 40° C. at 0.5° C./minute (6 cycles) | Type D |
| 2 | EtOH | Vapor Stress: 6 days at ambient and 24 hours at 40° C. | Type D + B |
| 3 | EtOH | Temperature Cycling: 40° C. for 120 minutes, cycle between 5° C. and 40° C. at 0.1° C./min (3 cycles) | Type D |
| 4 | EtOH | Slurry: ~2° C. for 5 days | Type D + H (disordered) |
| 5 | EtOH | Temperature Cycling: between 5° C. and 40° C. at 0.1° C./min (5 cycles) | Type D + H (disordered) |
| 6 | EtOH | Slurry: at~22° C. | Type D + H (disordered) |
| 7 | EtOH | Temperature Cycling: between 5° C. and 40° C. at 0.1° C./min (10 cycles) | compound 1 acetate EtOH solvate-Type E |
| 8 | EtOH | Vapor Stress: room temperature | Type D |
| 9 | EtOH | Recrystallization | XRPD amorphous compound 1 acetate + extra peaks at~5-10 °2θ-(similar to Type D + H) |
| 10 | EtOH/water | Precipitation with anti-solvent | compound 1 acetate EtOH solvate-Type E |
| 11 | EtOH | Recrystallization | compound 1 acetate EtOH solvate-Type E |
| 12 | EtOH | Slurry: room temperature | compound 1 acetate EtOH solvate-Type E |
| 13 | 95% v EtOH 5% v ACN/water (9:1 v/v) | Temperature Cycling | Type B |
| 14 | 90% v EtOH 10% v ACN/water (9:1 v/v) | Temperature Cycling | Type B |
| 15 | 95% v EtOH 5% v ACN/water (9:1 v/v) | Precipitation with anti-solvent | Type B |
| 16 | 95% v EtOH 5% v ACN/water (9:1 v/v) | Precipitation with anti-solvent | Type B |
| 17 | EtOH | Temperature Cycling | Type E |
| 18 | EtOH/water | Precipitation with anti-solvent | Type E |
| 19 | EtOH | Recrystallization | Type E |
| 20 | EtOH | Slurry: room temperature | Type E |
| 21 | ACN/EtOH/water (11.4:87.6:1 v/v/v) | Temperature Cycling | Type E |

TABLE 1-continued

| Entry No. | Solvent or Solvent Mixture | Screening method | XRPD Result |
|---|---|---|---|
| 22 | 85% v EtOH 15% v ACN/water (9:1 v/v) | Slurry: room temperature | Type E |
| 23 | EtOH/ACN (37:63 v/v, AEtOH~0.508) | Competitive slurry experiments with seeding | Type G + D |
| 24 | EtOH | Temperature Cycling | Type D + H (disordered) |

Figure 2:
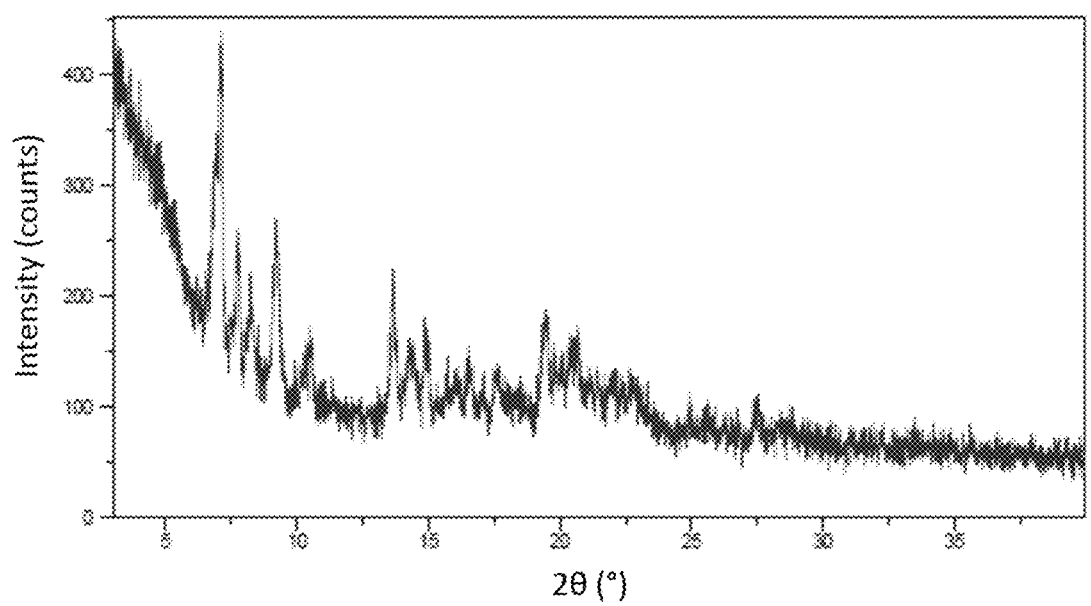
FIG. 2 is an image depicting X-ray powder diffraction (XRPD) pattern for Type A polymorph of compound 1 acetate.

Example 5. Further Characterization of Distinct Polymorphs of Compound 1 Acetate Type A Compound 1 acetate Type A was obtained via slurrying compound 1 acetate magnetically (1000 rpm) in EtOH at 40° C. for about five days. XRPD of compound 1 acetate Type A is shown in FIG. 2, DSC analysis indicated peak endotherms at 148.1 and 192.9° C. HPLC analysis confirmed the product was compound 1 acetate based on retention time. Purity by HPLC was unchanged from input material (99.1% pure).

Type B

Figure 3:
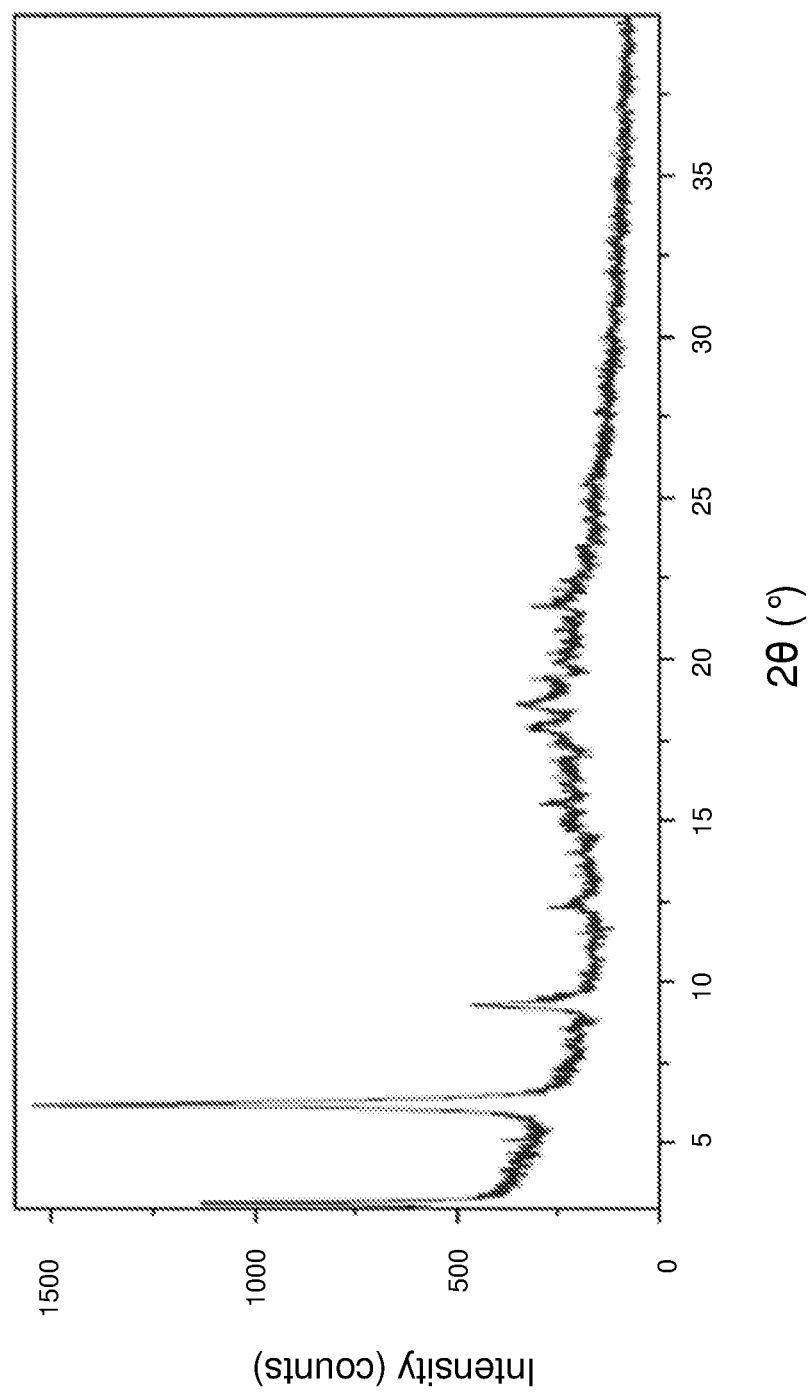
FIG. 3 is an image depicting the XRPD pattern for Type B polymorph of compound 1 acetate.

Compound 1 acetate Type B was prepared via slurrying compound 1 acetate in EtOH at room temperature for 5 days or heating-cooling between 40° C. and 5° C. in EtOH. XRPD of compound 1 acetate Type B is shown in FIG. 3. DSC analysis indicated peak endotherms at 128.7 and 183.4° C.

TG/DTA analysis of one sample of Type B material showed a weight loss of 8.74% between 27 and 77° C. Further weight loss above 160° C. may correspond with the onset of decomposition. A dynamic vapour sorption experiment of Type B material was performed. The sample was subjected to a step profile from 40-90% RH at 10% increments, followed by desorption from 90-0% RH at 10% increments and then adsorption from 0-40% RH at 10% increments. The material exhibits a gradual weight gain of 6% from 40-80% RH during the sorption isotherm. The desorption curve showed the material loses moisture rapidly between 90-80% RH and then more gradually between 80-0% RH. The final sorption curve exhibits a gradual uptake of moisture from 0-40% RH.

Compound 1 acetate Type B was analyzed by $^1$H NMR spectroscopy in MeOD-d4 and showed that ~0.5 molar equivalents of EtOH were present in the material. When slurrying compound 1 acetate Type B in EtOH at 40° C., no form transformation from compound 1 acetate Type B to compound 1 acetate Type A was observed after 3 days as indicated by XRPD characterization.

Compound 1 acetate Type B was successfully reproduced by slurrying compound 1 acetate for 35 mins in EtOH at RT by adding Type B seeds. In order to confirm the identity of Type B and rule out the possibility of it being degradation product(s), $^1$H NMR and HPLC characterization were performed. Negligible differences were observed between reproduced Type B material and the input material. The identification and purity of compound 1 acetate Type B was further verified by HPLC analysis (99.1% purity).

Type C

Figure 4:
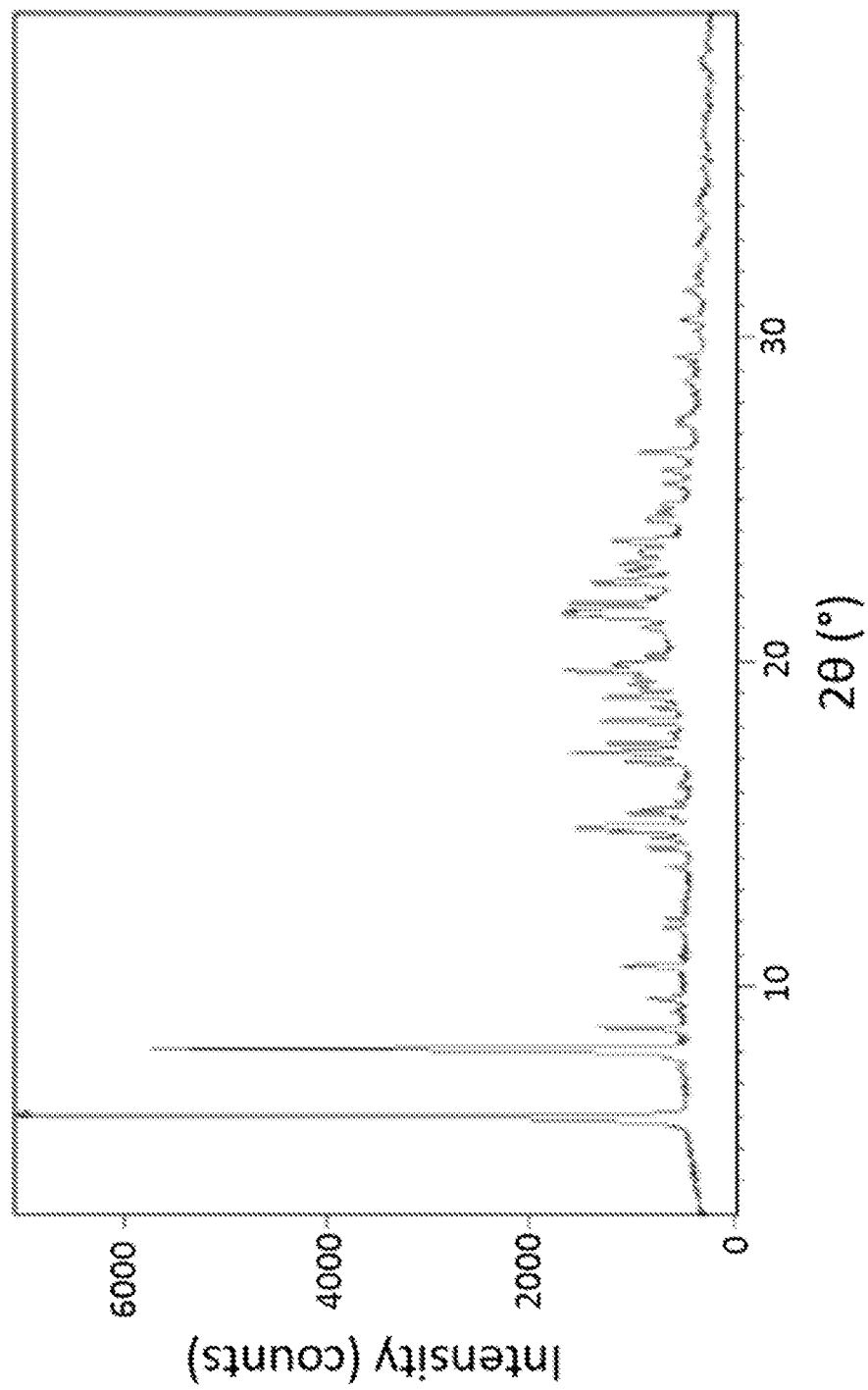
FIG. 4 is an image depicting the XRPD pattern for Type C polymorph of compound 1 acetate.

Compound 1 acetate Type C samples were obtained via slurrying compound 1 acetate (magnetically stirred at 1000 rpm) in 1,4-dioxane-N-methylpyrrolidinone (v/v; 9/1) at 40° C. and in 1,4-dioxane-N-methylpyrrolidinone (v/v; 4/1) at ambient temperature for about five days. XRPD pattern of Type C sample is shown in FIG. 4.

Type E

Compound 1 acetate Type E is an EtOH solvate that was formed by precipitation from EtOH/water, recrystallization from EtOH, and temperature cycling in EtOH. The material was designated as Form E based on its XRPD pattern.

TG/DTA analysis of compound 1 acetate Type E material showed weight losses of 10.38% from 27-80° C. and 8.53% from 80-114° C., both associated with endotherms in the DTA trace. Some of the weight loss could be due to surface adsorbed solvent. Further weight loss observed above 114° C. may correspond to the onset of decomposition.

A dynamic vapour sorption experiment of Type E material was performed. The sample was subjected to a step profile from 40 to 90% RH at 10% increments, followed by desorption from 90 to 0% RH at 10% increments and then adsorption from 0 to 40% RH at 10% increments. The isotherm showed the material exhibited a large weight loss (~18.5%) during the equilibration hold at 40% RH. This suggests that the material contains a lot of surface solvent which it loses during equilibration. The material exhibited a weight gain of 5% from 40-80% RH during the sorption isotherm. There was a larger weight gain above 80% RH.

Type E material (not dried) was analyzed by $^1$H NMR spectroscopy. The $^1$H NMR spectrum indicated that the compound contained ~9 molar equivalents of EtOH.

Reproducible methods to synthesize compound 1 acetate Type E are described below as method 1 and method 2.

Method 1

Figure 5:
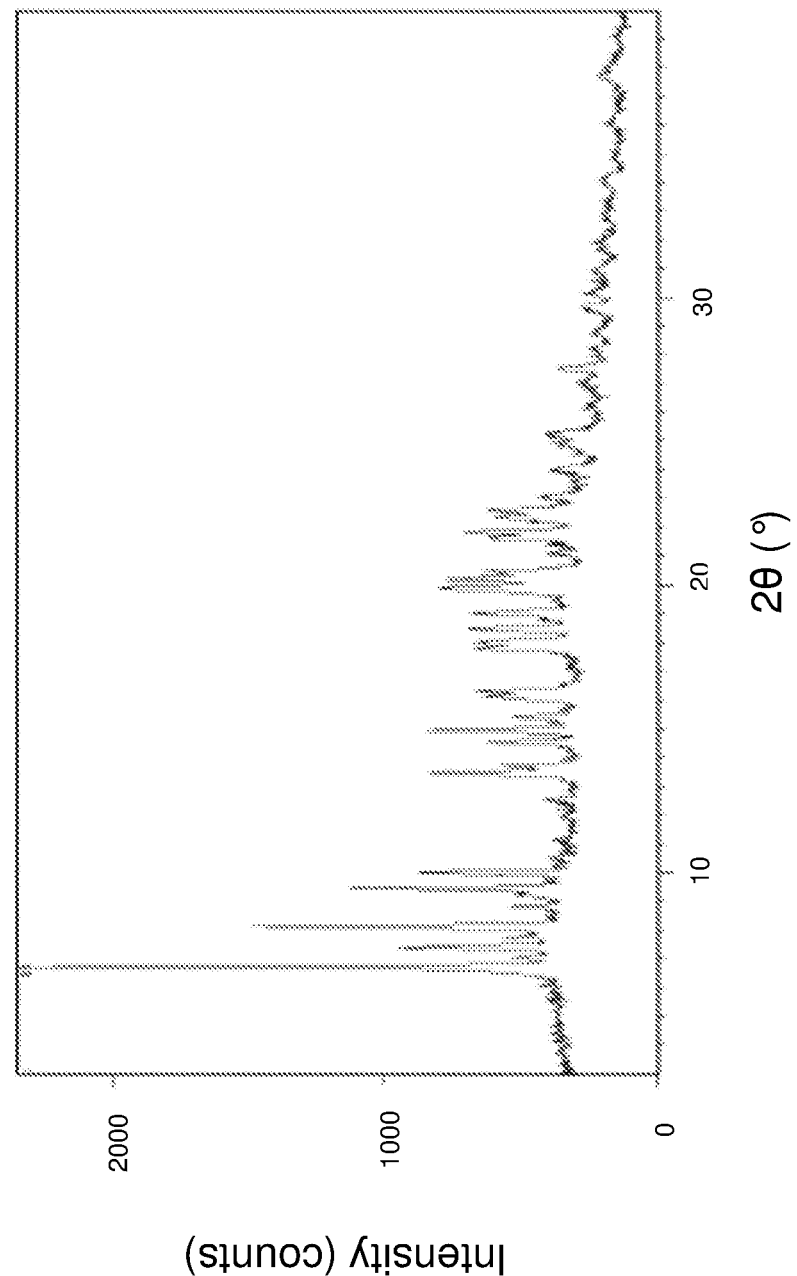
FIG. 5 is an image depicting the XRPD pattern for Type E polymorph of compound 1 acetate.

Amorphous compound 1 acetate (1 g) and EtOH (10 mL) were added to a vial and stirred for 20 minutes at ambient temperature (stirrer speed—300 rpm). Seeds of compound 1 acetate Type B (1-5 mg) were added, and the mixture was stirred at ambient for ~16 hours. The solids were isolated by centrifuge filtration (7 minutes at 3000 rpm) and analyzed by XRPD to confirm that the material was compound 1 acetate Type E (FIG. 5).

Method 2

A solution of compound 1 acetate (25 mg/mL) was prepared in 90:10% v/v EtOH/ACN mixtures with 3% water added. The solution was seeded with compound 1 acetate Type B and stirred for several days at 5° C. The isolated solids were collected and analyzed by XRPD and shown to be compound 1 acetate Type E.

Type D, Type G+D, and Type D+H

Figure 7:
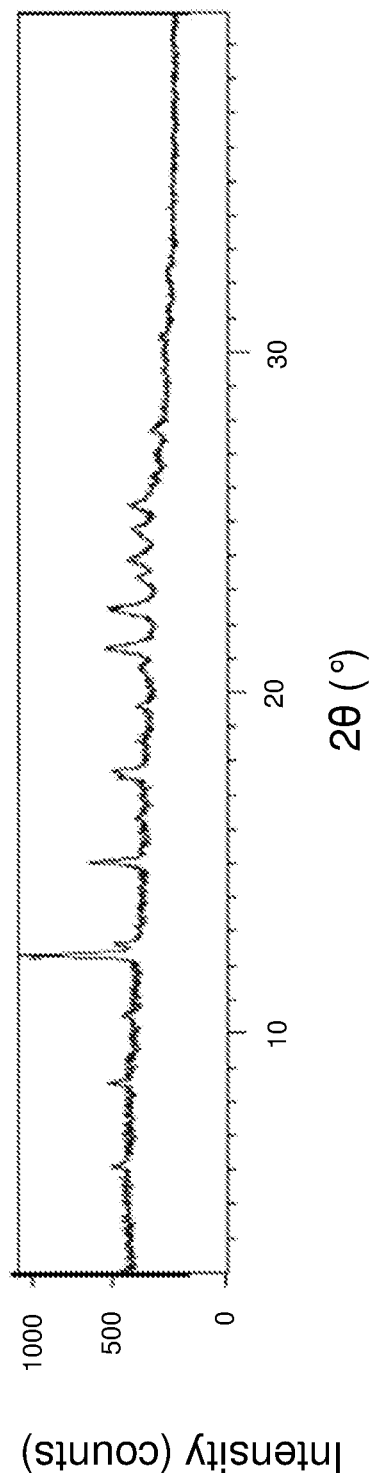
FIG. 7 is an image depicting the XRPD pattern for Type D polymorph of compound 1 acetate.

Compound 1 acetate Type D was obtained according to the method described in entries 1, 3, and 8 in Table 1. XRPD of compound 1 acetate Type D is shown in FIG. 7.

Figure 8:
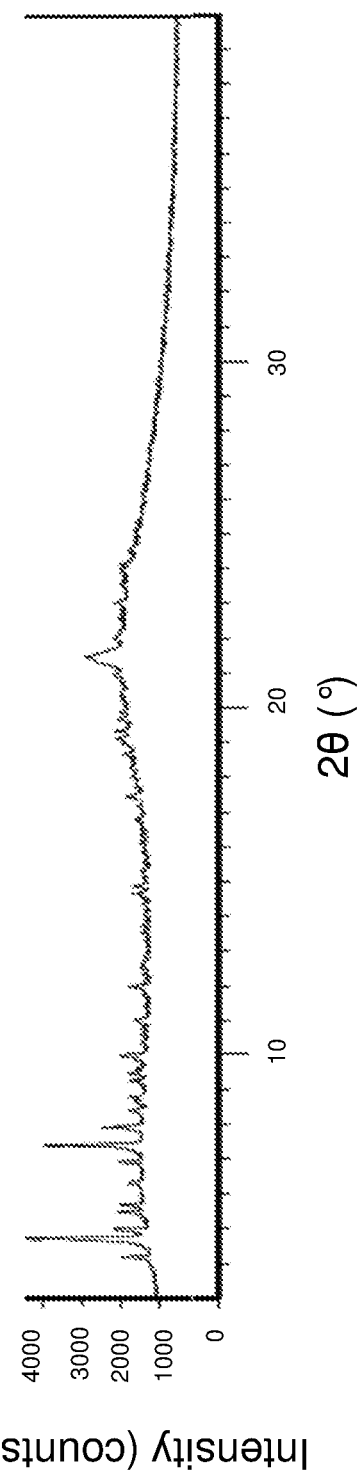
FIG. 8 is an image depicting the XRPD pattern for Type G+D polymorph of compound 1 acetate.

Compound 1 acetate Type G+D was obtained according to the method described in entry 23 in Table 1. XRPD of compound 1 acetate Type G+D is shown in FIG. 8.

Figure 9:
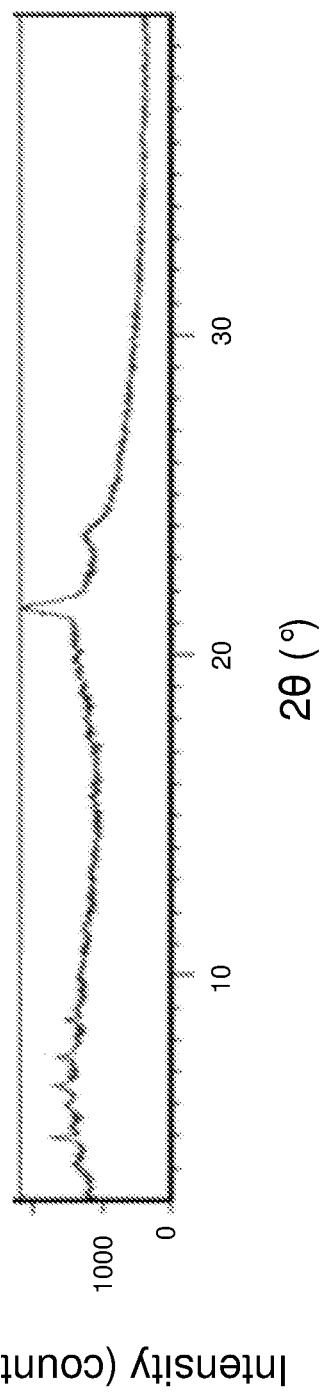
FIG. 9 is an image depicting the XRPD pattern for Type D+H polymorph of compound 1 acetate.

Compound 1 acetate Type D+H was obtained according to the method described in entries 4-6, 9, and 24 of Table 1. XRPD of compound 1 acetate Type D+H is shown in FIG. 9.

Example 6. Preparation of Type B by Drying Type E

Compound 1 acetate Type E is a metastable solvate and converts to compound 1 acetate Type B on drying or storage at low ethanol activity (aEtOH<0.2). Type E was stable at an EtOH activity of >0.8.

Figure 6:
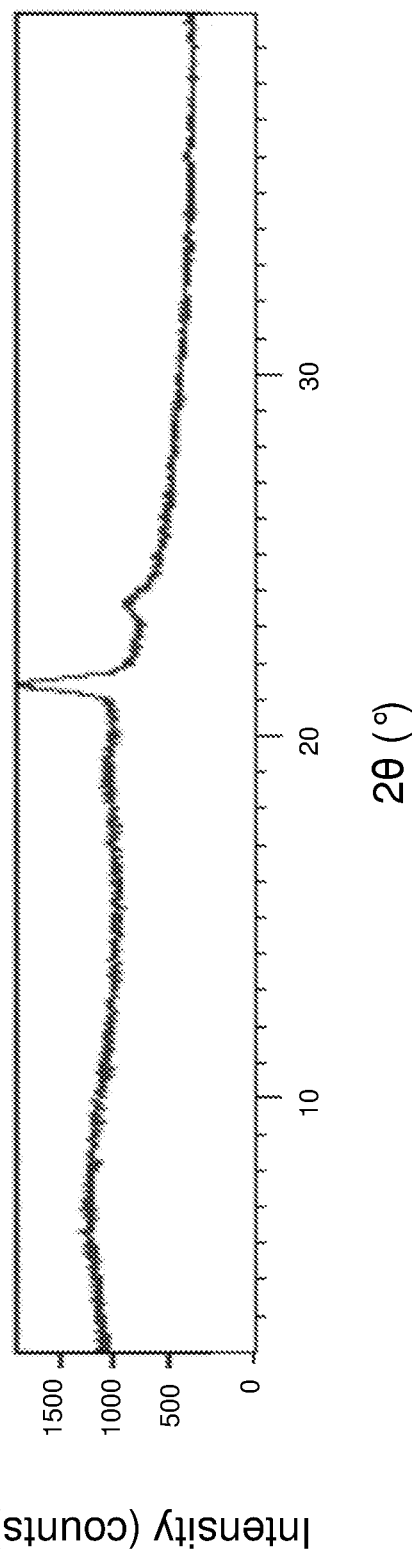
FIG. 6 is an image depicting the XRPD pattern for Type B polymorph of compound 1 acetate that was prepare by drying a sample of Type E polymorph of compound 1 acetate.

Compound 1 acetate Type E (1 g) was added to a beaker and dried in the vacuum oven at 40° C. overnight (not more than 18 hours). The solid was analyzed by XRPD analysis and shown to be Type B (FIG. 6).

Four samples of compound 1 acetate Type E were added to vials and placed in a desiccator, under vacuum, for up to 7 days. Samples were analyzed periodically by XRPD and the results are shown in Table 2. These results show that Type E was stable for up to 4 hours at ambient temperature in the desiccator. The X-ray diffractogram showed a mixture of Types B and E after 1 day with complete conversion to Type B observed within 5 days.

TABLE 2

| Input | Entry No. | Conditions | Result | XRPD Result |
|---|---|---|---|---|
| Type B | 25 | Ambient conditions* for 5 days | solid | Type B |
| Type E | 26 | Ambient conditions* for 5 days | solid | Type B |
| Type E | 27 | Desiccator at ambient conditions* for 4 hours | solid | Type E |
| Type E | 28 | Desiccator at ambient conditions* for 1 day | solid | Type B + Type E |
| Type E | 29 | Desiccator at ambient conditions* for 5 days | solid | Type B |
| Type E | 30 | Desiccator at ambient conditions* for 7 days | solid | Type B |

*ambient conditions (44-63% RH, 20-25° C.)

Example 7. Crystallization Experiments

2% Water in EtOH/Acetonitrile

Solutions of amorphous compound 1 acetate were prepared in the EtOH/acetonitrile mixtures with 2% water. The samples were seeded with Type B compound 1 acetate and stirred for several days at 5° C. The results are shown in Table 3. Types B and E, or mixtures of the two, were isolated from most of the crystallization experiments.

TABLE 3

| Entry No. | Concentration (mg/mL) | EtOH:ACN ratio | Conditions | Result | XRPD Result |
|---|---|---|---|---|---|
| 31 | 60 | 75:25 | Seeded with Type B | Precipitated | E + B |
| 32 | 60 | 90:10 | Slurried at 5° C. | Not soluble | E |
| 33 | 60 | 50:50 | Seeded with Type B | Precipitated | E + B |
| 34 | 25 | 75:25 | Seeded with Type B; stirred at 5° C. overnight | Precipitated after seeding | Amorphous |
| 35 | 25 | 90:10 | Seeded with Type B | Precipitated | E |
| 36 | 25 | 50:50 | Seeded with Type B; stirred at 5° C. | No solids formed | |

1% Water in EtOH/Acetonitrile

Crystallization experiments were carried out with amorphous compound 1 acetate and ethanol/acetonitrile mixtures with 1% water (Table 4). The experiment with 90% ethanol did not form a solution, even on dilution to 50 mg/mL. A solid precipitated in the crystallization experiment with 75% EtOH before seeding had taken place. Both of these experiments yielded Type E compound 1 acetate. The solid isolated from the experiment in EtOH:acetonitrile (50:50) deliquesced prior to x-ray analysis.

TABLE 4

| Entry No. | Concentration (mg/mL) | EtOH:ACN ratio | Conditions | Results | XRPD Result |
|---|---|---|---|---|---|
| 37 | 60 | 75:25 | | Precipitate | Type E |
| 38 | 60→50 | 90:10 | Slurried | Not soluble | Type E |
| 39 | 60 | 50:50 | Seeded with Type B; stirred at 5° C. overnight | | Deliquesced |

Anhydrous in EtOH/Acetonitrile

Solutions of amorphous compound 1 acetate were prepared in the EtOH/acetonitrile mixtures (Table 5). Many samples yielded either Type E or a mixture of Types E and B.

TABLE 5

| Entry No. | Concentration (mg/mL) | EtOH:ACN ratio | Conditions | Results | XRPD Result |
|---|---|---|---|---|---|
| 40 | 20 | 75:25 | Seeded with Type B and stirred at 5° C. | Soluble | Poor signal |
| 41 | 20 | 90:10 | Stirred at room temperature | Precipitated before seeding | Type E |
| 42 | 20 | 50:50 | Seeded with Type B and stirred at 5° C. | Soluble | Poor signal |
| 43 | 40 | 75:25 | Seeded with Type B and stirred at 5° C. | Soluble | Type E |
| 44 | 40 | 90:10 | Stirred at room temperature | Precipitated before seeding | Type E |
| 45 | 40 | 50:50 | Seeded with Type B and stirred at 5° C. | Soluble | Mxiture of amorphous, Type E, and unknown |
| 46 | 60 | 75:25 | Stirred at room temperature | Precipitated before seeding | Type E + B |
| 47 | 60 | 90:10 | Stirred at RT | Precipitated before seeding | Type B |
| 48 | 60 | 50:50 | Slurried at room temperature | Not soluble | |

Example 8. Purification by Crystallization

Material containing high levels of compound 1 acetate beta-diastereomer as an impurity was studied to understand the potential for purity upgrade of compound 1 acetate via crystallization. Crude, amorphous compound 1 acetate containing 14% compound 1 acetate beta-diastereomer (~200 mg) was stirred in ethanol for 18 hours. After filtration, the solids were determined to be compound 1 acetate Type E polymorph by XRPD analysis. HPLC analysis of the material showed a compound 1 acetate beta-diastereomer content of 7.6%. This material was re-slurried and the compound 1 acetate beta-diastereomer content dropped to 6.5%. Further experiments were carried out using samples with less compound 1 acetate beta-diastereomer content and the results are shown in Table 6. In all cases, the compound 1 acetate beta-diastereomer content decreased after slurrying in ethanol. An ethanol slurry may be a useful method for reducing the β-isomer content and thereby, increasing the purity of compound 1 acetate.

TABLE 6

| Entry No. | Condition | Beta-diastereomer Content Before | Beta-diastereomer Content After |
|---|---|---|---|
| 49 | EtOH slurry for 1 day | 14% | 7.6% |
| 50 | EtOH re-slurry for 2 days | 7.6% | 6.5% |
| 51 | EtOH slurry for 1 day | 1.5% | 1.2% |
| 52 | EtOH slurry for 1 day | 4.1% | 2.7% |
| 53 | EtOH slurry for 1 day with 0.5% water | 4.1% | 2.8% |
| 54 | Temperature Cycling | 14% | 9.1% |

Example 9. Synthesis of Compound 1 Acetate from the 3,4-Dimethoxyphenylboronate Ester of Anidulafungin and Isolation of Compound 1 Acetate by Precipitation Choline Chloride Drying Choline chloride (185 g) was suspended in 2-MeTHF (500 ml) and stirred for 1 hour at room temperature. The solvent was removed under vacuum to near-dryness then dried under vacuum at 70-75° C. for 1 hour.

Anidulafungin Boronate Ester Preparation

Anidulafungin (50 g), 3,4-dimethoxyphenylboronic acid (10.37 g), and tetrahydrofuran (250 ml) were charged in a 1000 mL round bottom flask. The suspension was stirred at room temperature for 1.5 hours. The solvent was removed under vacuum. The resulting solid was solubilized in 2-MeTHF (400 mL) and the solvent was evaporated under vacuum. This process was repeated one more time.

Conjugation

Dried choline chloride (73.6 g), acetonitrile (200 mL) and trifluoroacetic acid (48 mL) were combined. The suspension was stirred for 10 min. In a second reactor, dried anidulafungin boronate ester (25.6 g) and dry THF (150 mL) were combined and stirred at room temperature until the material was completely solubilized (30 minutes). The acidic solution of choline chloride was added to the stirred boronate ester solution over 30 minutes. The resulting suspension was stirred for 3 hours at room temperature then cooled to 0° C. and quenched by addition of 70/30 water:acetonitrile mixture (560 mL). The pH of the crude reaction mixture was adjusted within the 2.0-2.2 range by slow addition of chilled half-dilute ammonium hydroxide solution (typically 80-82 mL). The crude solution was diluted to a final volume of 2000 mL with 70/30 water:acetonitrile solution. The beta-diastereomer content of the crude solution was 3.7% and the epimer content was 0.43%.

After synthesis of the crude mixture, compound 1 acetate was purified using a reversed phase C18 silica media, with the product eluted from the column using an aqueous acetonitrile gradient. Final pools of the appropriate purity were brought forward to an on-column concentration using the same media to generate a concentrated solution.

Post concentration, compound 1 acetate solution was concentrated via acetonitrile removal under reduced pressure. This solution was then used for the following isolation examples.

Isolation Method 1

To the resulting concentrate was added an equal volume of 1.5M ammonium acetate. The aqueous solution was extracted with 1-BuOH (2×0.5 vol). Nearly 100% of compound 1 acetate was extracted into the alcohol layer which contained about 20% water. The 1-BuOH solution was azeotropically dried and concentrated. Compound 1 acetate began to precipitate during the drying/concentration process. MTBE was added to complete precipitation. The product was filtered and dried. Isolated product contained 5.8% acetate (theory 4.6%).

Isolation Method 2

To a 10 mL solution of compound 1 acetate (30 mg/mL, 8:2 water/acetonitrile, pH 5.9) was added 10 mL of 2.5M aq. sodium acetate and 10 mL methyl ethyl ketone. The mixture was mixed, then the layers allowed to settle. The bottom aq. layer was discarded. The organic layer was azeotropically dried by vacuum distillation while maintaining a constant volume by adding back methyl ethyl ketone. The precipitated solids were filtered and dried to provide 156 mg of compound 1 acetate.

Isolation Method 3

To a 10 mL solution of compound 1 acetate (30 mg/mL, 8:2 water/acetonitrile, pH 5.9) was added 10 mL of 2.5M aq. sodium acetate and 10 mL of 2-methyltetrahydrofuran. The mixture was mixed, then the layers allowed to settle. The bottom aqueous layer was discarded. The organic layer was azeotropically dried by vacuum distillation while maintaining a constant volume by adding back 2-methyltetrahydrofuran. The precipitated solids were isolated by centrifugation, titurated with MTBE, filtered and dried to provide 152 mg of compound 1 acetate.

Isolation Method 4

To a 20 mL solution of compound 1 acetate (7.4 mg/mL in water) was added 10 mL of 2.6M ammonium acetate and 6 mL of 1-BuOH. After mixing, the layers were allowed to settle and separated. The aq. layer was back extracted with 4 mL of 1-BuOH, mixed, settled, and layers separated. The organic layers were combined, then concentrated under vacuum to 6.5 mL. MTBE was added to induce precipitation. After filtration and drying, 144 mg of compound 1 acetate was recovered.

Isolation Method 5

To a 5 mL solution of compound 1 acetate was added 5 mL of isobutyl alcohol and 5 mL of 2.5 M ammonium acetate (pH 5.2) solution. The mixture was mixed and then allowed to settle. The organic phase was separated and KF measured to show that the water content was 15.54%. The organic phase was reduced in volume and the distillate replaced in order to keep a constant volume, and during this process solids began to precipitate. The solids were isolated by centrifugation. The solids were further washed with 2×1 vol of isobutyl alcohol and dried under vacuum to give a white solid (142 mg, 20.9% w/w residual solvent). A sample was taken and washed with MTBE and dried under vacuum giving 1.20% w/w of MTBE and 0.55% w/w residual isobutyl alcohol.

Isolation Method 6

To a 25 mL solution (50 mg/mL of compound 1 acetate) was added isobutyl alcohol (25 ml) and 2.5M $NH_4OAc$ solution [pH 5.26] (25 mL). The extraction mixture was stirred for 15 minutes before the stirring stopped and the phases allowed to split (settled after 4 minutes). The organic extract was concentrated with replacement of fresh solvent in order to azeotrope the organic phase, resulting in precipitation of a white solid. A white solid (1.47 g) was recovered by centrifugation. Then 500 mg of this material was added to a flask and placed on a rotavap with a water bath at 25° C. Nitrogen gas was bubbled through a dreschel bottle containing water and the wet nitrogen then piped directly into the flask. $^1H$ NMR data indicated that there was no residual isobutyl alcohol in the sample after drying.

OTHER EMBODIMENTS

All publications, patents, and patent applications mentioned in this specification are herein incorporated by reference to the same extent as if each independent publication or patent application was specifically and individually indicated to be incorporated by reference.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure that come within known or customary practice within the art to which the disclosure pertains and may be applied to the essential features hereinbefore set forth, and follows in the scope of the claims. Other embodiments are within the claims.

The invention claimed is:

1. A solid crystalline form of compound 1 acetate having an X-ray powder diffraction (XRPD) pattern comprising angles 2θ (°) of 7.1±0.2, 9.2±0.2, and 13.7±0.2.

2. A solid crystalline form of compound 1 acetate having an X-ray powder diffraction (XRPD) pattern comprising angles 2θ (°) of 7.1±0.2, 9.2±0.2, and 13.7±0.2 and one or more angles 2θ(°) selected from the group consisting of 7.8±0.2, 8.3±0.2, 10.5±0.2, 14.9±0.2, 16.6±0.2, 17.6±0.2, 19.4±0.2, 20.5±0.2, 22.7±0.2, and 27.5±0.2.

3. A solid crystalline form of compound 1 acetate having an X-ray powder diffraction (XRPD) pattern comprising angles 2θ (°) of 6.8±0.2, 7.4±0.2, 8.2±0.2, and 9.5±0.2 and one or more angles 2θ (°) selected from the group consisting of 10.1±0.2, 13.5±0.2, 15.0±0.2, 20.0±0.2, 20.3±0.2, and 21.9±0.2.

4. A solid crystalline form of compound 1 acetate having an X-ray powder diffraction (XRPD) pattern comprising angles 2θ (°) of 3.2±0.2 and 6.2±0.2 and one or more angles 2θ (°) selected from the group consisting of 9.3±0.2, 12.3±0.2, 15.5±0.2, 17.9±0.2, 18.5±0.2, 19.4±0.2, and 21.6±0.2.

5. A solid crystalline form of compound 1 acetate having an X-ray powder diffraction (XRPD) pattern comprising angles 2θ (°) of 6.0±0.2 and 8.7±0.2 and one or more angles 2θ (°) selected from the group consisting of 10.6±0.2, 14.7±0.2, 14.9±0.2, 15.3±0.2, 15.5±0.2, 17.2±0.2, 18.9±0.2, 19.7±0.2, 20.0±0.2, 21.5±0.2, 21.6±0.2, 21.8±0.2, 22.4±0.2, and 23.7±0.2.

* * * * *